US00PP16875P2

(12) United States Plant Patent
Pieters

(10) Patent No.: US PP16,875 P2
(45) Date of Patent: Jul. 25, 2006

(54) ***CHRYSANTHEMUM* PLANT NAMED 'GEDI THREE SIE'**

(50) Latin Name: *Chrysanthemum morifolium*
Varietal Denomination: Gedi Three Sie

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 0 days.

(21) Appl. No.: 11/107,645

(22) Filed: Apr. 14, 2005

(51) Int. Cl.
*A01H 5/00* (2006.01)

(52) U.S. Cl. ..... Plt./290

(58) Field of Classification Search ..... Plt./290
See application file for complete search history.

(56) References Cited

U.S. PATENT DOCUMENTS

PP13,796 P2 5/2003 Pieters
PP14,403 P2 12/2003 Pieters

*Primary Examiner*—Kent Bell
*Assistant Examiner*—Annette H Para
(74) *Attorney, Agent, or Firm*—Knobbe Martens Olson & Bear, LLP

(57) ABSTRACT

A new and distinct *Chrysanthemum* plant cultivar is disclosed, characterized by a gold/bronze colored flower with darker center. The plant has a round, mounding plant shape and naturally blooms in the last two weeks of August.

1 Drawing Sheet

Figure 1:
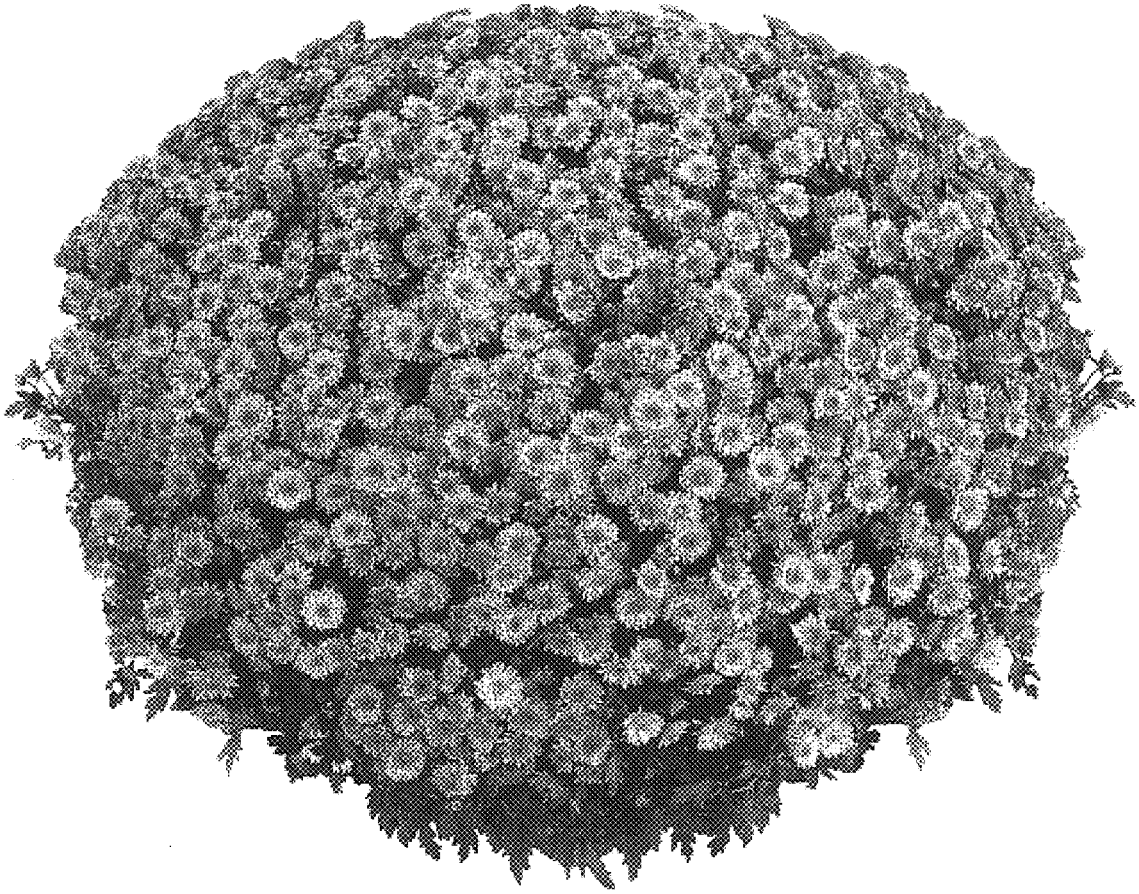

Latin name of the genus and species: *Chrysanthemum morifolium.*
Variety denomination: 'Gedi Three Sie'.

BACKGROUND OF THE INVENTION

The new cultivar is a product of hybridization of a female parent *Chrysanthemum* plant variety 'Tr/96 AF 06' (unpatented, undistributed seedling) and a male parent *Chrysanthemum* plant variety 'Weiss' (unpatented, undistributed in the U.S.). The new cultivar was discovered and selected by Dirk Pieters in a controlled environment in Oostniewkerke, Belgium, during September, 1997.

A sexual reproduction of the new cultivar 'Gedi Three Sie' by terminal cuttings and tissue culture was performed in Oxnard, Calif., and has shown that the unique features of this cultivar are stable and reproduced true to type on successive generations.

SUMMARY OF THE INVENTION

The cultivar 'Gedi Three Sie' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Gedi Three Sie.' These characteristics in combination distinguish 'Gedi Three Sie' as a new and distinct *Chrysanthemum* cultivar:

1. The plant has a gold/bronze colored flower with darker center.
2. The plant has a round, mounding plant shape.
3. The plant is free branching.
4. The plant vigor is average.

5. The plant naturally blooms in the last two weeks of August.

Plants of the new cultivar 'Gedi Three Sie' are similar to plants of the female parent variety, 'Tr/96 AF 06,' in most horticultural characteristics. However, plants of the new cultivar have longer lasting flowers, with bronze ray florets, rather than the yellow ray florets of the female parent. Additionally, plants of the new cultivar 'Gedi Three Sie' are shorter than plants of the female parent variety.

Plants of the new cultivar 'Gedi Three Sie' are similar to plants of the male parent variety, 'Weiss,' in most horticultural characteristics. However, plants of the new cultivar have a longer lasting, smaller diameter flower than plants of the male parent variety. Plants of the new cultivar are also shorter than plants of the male parent variety.

In comparison to the commercially available variety 'Gedi One Nov' (U.S. Plant Pat. No. 13,796), 'Gedi Three Sie' has a smaller diameter flower with fewer ray florets. The new variety also has about 12 more flowers per flowering branch than the comparable variety 'Gedi One Nov,' The new variety 'Gedi Three Sie' also has shorter but wider leaves in comparison to 'Gedi One Nov.'

In comparison to the commercially available variety 'Gedi Two Fig' (U.S. Plant Pat. No. 14,403), the new variety 'Gedi Three Sie' has a larger diameter flower and about 11 more flowers per flowering branch. Additionally, the floral longevity of the new variety 'Gedi Three Sie' is about eight days longer than the floral longevity of the comparable variety 'Gedi Two Fig.'

BRIEF DESCRIPTION OF THE PHOTOGRAPH

The accompanying photograph in FIG. 1 illustrates in full color a typical plant of 'Gedi Three Sie' grown in a 2 gallon container. One cutting was used in the pot. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'Gedi Three Sie' plants grown in a greenhouse in Oxnard, Ventura County, Calif., during the month of September 2003. The growing temperature ranged from about 12° C. to 15° C. at night to about 12° C. to 20° C. during the day. Measurements and numerical values represent averages of typical flowering types, and are believed to apply to plants of the variety grown under similar conditions of soil and climate elsewhere:

Botanical classification: *Chrysanthemum morifolium* 'Gedi Three Sie.'
Commercial classification: Garden-type Chrysanthemum.

PROPAGATION

Time to rooting: 7 to 14 days at approximately 21° C.
Root description: Fine, fibrous.

PLANT

Growth habit: Mounding herbaceous perennial.
Height: Approximately 30.5 cm.
Plant spread: Approximately 35 cm.
Growth rate: Moderate.
Branching characteristics: Free branching.
Length of lateral branches: Approximately 26 cm.
Number of leaves per lateral branch: Approximately 19.
Age of plant described: Approximately 135 days from a rooted cutting.

FOLIAGE

Leaf:
- *Arrangement.*—Alternate.
- *Average length.*—Approximately 6.7 cm.
- *Average width.*—Approximately 5.3 cm.
- *Shape of blade.*—Ovate.
- *Apex.*—Cuspidate.
- *Base.*—Attenuate.
- *Attachment.*—Stalked.
- *Margin.*—Palmately lobed and toothed.
- *Texture of top surface.*—Lightly pubescent.
- *Texture of bottom surface.*—Lightly pubescent.
- *Leaf internode length.*—Approximately 2.7 cm.
- *Color.*—Young foliage upper side: Near Green 138A. Young foliage under side: Near Green 138A. Mature foliage upper side: Near Green 137A. Mature foliage under side: Near Green 137B.
- *Leaf venation.*—Venation type: Palmately-veined Venation color upper side: Near Green 137B. Venation color under side: Near Green 138A.

Petiole:
- *Average length.*—Approximately 2.3 cm
- *Color.*—Near Green 137B.
- *Diameter.*—Approximately 0.2 cm.

BLOOM

Flower:
- *Flowering habit.*—Induced by darkness period greater than approximately 13.5 hours, approximately 45 days of appropriate day length required to induce and develop blooms.
- *Form.*—Decorative.
- *Natural flowering season.*—Approximately the last week of August through the first week of September.
- *Number of flowers per lateral branch.*—Approximately 26.
- *Diameter.*—Approximately 5.3 cm.
- *Depth.*—Approximately 2.3 cm.
- *Longevity on plant.*—Approximately 29 days.
- *Persistence.*—Persistent.

Ray florets:
- *Appearance.*—Matte.
- *Texture.*—Smooth.
- *Average number of ray florets per flower.*—Approximately 160.
- *Shape.*—Oblong.
- *Aspect.*—Flat.
- *Margin.*—Entire.
- *Apex.*—Retuse.
- *Length.*—Approximately 2.5 cm.
- *Width.*—Approximately 0.8 cm.
- *Color.*—Upper surface at first opening: Near Greyed-orange 175B. Upper surface at maturity: Near Yellow-orange 20A. Upper surface at fading: Near Yellow 10B. Under surface at first opening: Near Yellow 12B. Under surface at maturity: Near Yellow-orange 21C. Under surface at fading: Near Yellow-orange 17D.

Disc florets:
- *Appearance.*—Shiny.
- *Texture.*—Smooth.
- *Average number of disc florets per disc.*—Approximately 10.
- *Shape.*—Cylindric.
- *Apex.*—Obtuse.
- *Average length.*—Approximately 0.7 cm.
- *Average width.*—Approximately 0.1 cm.
- *Color.*—At first opening: Near Yellow-orange 17C. At maturity. Near Yellow-orange 16C. At fading: Near Yellow-orange 20A.

Peduncle:
- *Length.*—At terminal end (shortest): Approximately 2.4 cm. At lateral end (longest): Approximately 6.4 cm.
- *Angle to stem.*—Acute.
- *Strength.*—Moderate.
- *Color.*—Near Green 137A.
- *Habit.*—Upright.
- *Diameter.*—Approximately 0.2 cm.
- *Surface texture.*—Light pubescent.

Flower bud:
- *Length.*—Approximately 0.9 cm.
- *Diameter.*—Approximately 0.8 cm.
- *Form.*—Globular.
- *Color.*—Near Greyed-orange 172A.

Involucral bracts (phyllaries):
- *Appearance.*—Matte.
- *Texture.*—Lightly pubescent.
- *Number.*—Approximately 24.
- *Shape.*—Oblanceolate.
- *Margin.*—Entire.
- *Apex.*—Acute.
- *Length.*—Approximately 0.9 cm.
- *Width.*—Approximately 0.8 cm.
- *Color.*—Upper side: Near Green 137A. Under side: Near Green 137A.

REPRODUCTIVE ORGANS

Ray florets:

*Number of pistils per floret.*—1.
*Stigma shape.*—branched.
*Stigma color.*—Near Yellow 3A.
*Style color.*—Near Yellow 2A.
*Style length.*—Approximately 0.7 cm.
*Stamens.*—Absent.

Disc florets:

*Number of pistils per floret.*—1.
*Stigma shape.*—Two-branched.
*Stigma color.*—Near Yellow 2C.
*Style length.*—Approximately 0.3 cm.
*Style color.*—Near Yellow-green 154D.
*Number of stamens per floret.*—Approximately 5.
*Anther shape.*—Tubular.
*Anther color.*—Near Yellow 8A.
*Pollen color.*—Near Yellow 9A.

OTHER CHARACTERISTICS

Disease resistance: Neither resistance nor susceptibility has been observed in this variety.

Drought tolerance/cold tolerance: Flowering plants are hardy to a low temperature of about −2° C. Non-flowering plants are hardy in the approximate range of 3° C. to −6° C., depending upon duration of cold an amount of moisture in the soil. With adequate water plants are hardy to a high temperature of about 45° C.

Fruit/seed production: Commercially, this plant is not used or observed in a stage wherein seeds would be produced. Therefore, seed production has not been observed.

What is claimed is:

1. A new and distinct cultivar of *Chrysanthemum* plant named 'Gedi Three Sie' as herein illustrated and described.

* * * * *